United States Patent
Tsai et al.

(10) Patent No.: US 6,586,016 B1
(45) Date of Patent: Jul. 1, 2003

(54) ST 188L AS THE PREVENTION AND TREATMENT FOR CANCERS AND INFECTIONS

(75) Inventors: Yi Ming Tsai, Taipei (TW); Kou Mark Hwang, Taipei Shien (TW); Suying Liu, Taipei Shien (TW)

(73) Assignee: Sagittarius Life Science Corp., Taipei Shien (TW)

( * ) Notice: Subject to any disclaimer, the term of this patent is extended or adjusted under 35 U.S.C. 154(b) by 0 days.

(21) Appl. No.: 09/952,288

(22) Filed: Sep. 13, 2001

(51) Int. Cl.⁷ .............................................. A61K 35/78
(52) U.S. Cl. ..................................................... 424/725
(58) Field of Search ............................... 424/195.1, 725

(56) References Cited

U.S. PATENT DOCUMENTS 5,602,170 A * 2/1997 Chang et al. ................ 514/444
5,817,297 A * 10/1998 Ha et al. ....................... 424/58

* cited by examiner

Primary Examiner—Christopher R. Tate
Assistant Examiner—Patricia Patten
(74) Attorney, Agent, or Firm—Chi Ping Chang; Pacific Law Group LLP

(57) ABSTRACT

The present invention provides Chinese herbal compositions, ST 188L and method for prevention and treatment of cancers and infectious diseases. The Chinese herbal compositions comprise a formulation prepared ratably from a group of herbal plants consisting essentially of *Ecchinops grijissii, Cirsium segetum* Bge, *Solanum indicum* Linn, *Lonicerae flos*, and *Zizyphi fructus*. ST188L appeared to be activated in vivo to stimulate the activity of NK cells and LAK cells as shown by the increases in cytolytic activity of peripheral blood mononuclear cells isolated from volunteers after intake of ST 188L toward target cells, such as K562, Daudi, HepG2 and HBV transfected HepG2-2215 in a dose dependent manner. ST 188L has been proven to be effective on eradicating malignancy in a cancer patient by enhancing said patients' endogenous immune system to keep said patient cancer free for more than ten years.

15 Claims, 11 Drawing Sheets

ST 188L AS THE PREVENTION AND TREATMENT FOR CANCERS AND INFECTIONS

FIELD OF INVENTION

This invention is in the field of medicinal prevention and treatment of cancers and infections. In particular, it relates to a Chinese herbal formulation, ST 188L, and a method for the prevention and treatment of cancers and infections that comprises administering an effective dose of the herbal formulation. The raw materials for such formulation are *Ecchinops grijissii, Cirsium segetum* Bge, *Solanum indicum* Linn, *Lonicerae flos*, and *Zizyphi fructus*.

BACKGROUND OF INVENTION

Cancer is the second leading cause of death, next to cardiovascular disease, in the US. According to WHO, there are 31 million cancer sufferers worldwide, 10 million new cases, and 7 million die of it each year. The medical cost, care cost, and society cost are difficult to be estimated. Investigators continue to search for new therapeutic strategies for cancers.

The pathological and molecular mechanisms for cancer initiation and promotion have been revealed after decades of researches. There are many genes involved in the initiation and progression of cancers, some are oncogenic and some are tumor suppressive. Genetic, endocrinologic, immunologic, and environmental factors intertwine in the process of transformation and progression. Cancers are diseases caused by multi-factors under complex mechanisms.

The control and cure of cancers remain to be one of the most challenging health care tasks. Current modalities of therapies for cancers include surgery, radiotherapy, chemotherapy, gene therapy, immune therapy, or a combination of any of these treatments. Although surgery is the most effective way to eradicate tumor, when the patients are diagnosed with cancers, their tumors have substantially become inoperable. Current radiotherapy and chemotherapy modalities are unable to discriminate normal cells from neoplastic cells; therefore, there are apparent dose-limiting toxicities. Gene therapy is still at very early stage of clinical practice. Lately, immune therapy has shown very promising results.

Cancer cells are vulnerable to immune effector cells such as macrophages, natural killer cells (NK cells), and cytotoxic T lymphocytes (Vujanovic N L, Yasumura S, and Hirabayashi H., J. Immunol 1995; 154:281–9; Kuge S, Miura Y, Nakamura Y, Mitomi T, Habu S, and Nishimura T., J. Immunol 1995; 154:1777–85; and Nabioullin R, Sone S, Mizuno K:, J Leukocyte Biol 1994; 55:437–42. However, lymphocyte functions are suppressed in patients with cancer and in animal tumor models (Chouaib S, Asselin-Paturel C, Mami-Chouaib F, Caignard A., Immunol Today 1997; 18:493–7; and Wojtowiczpraga S., J. Immunother 1997; 20:165–77.). A reduction in immune competence due to suppressor cells including inhibitory T cells, macrophages, and immature bone marrow nonspecific suppressive cells has been correlated with reduced survival of patients and animals with cancer (Kaffenbeerger W, Holzer-Muller L, Auberger T, Clasen B P, Hohlmeier G, and van Beuningen D., Strahlenther Onkol 1995; 171:444–53; Aoe T, Okamoto Y, and Saito T., J. Exp. Med. 1995; 181:1881–6; and Young M R I, Schmidt-Pak A, Wright M A, Matthews J P, Collins S L, and Petruzzelli G., Clin Cancer Res.1995; 1:95–103).

The induction and enhancement of immune activity most likely would have impact on cancer therapy. Most of the cancer patients eventually die of tumor metastasis. Many evidences demonstrate that NK cells and cytokines produced by NK cells inhibited tumor metastasis (Smyth M J, et al., J. Immunol. 1999; 162: 6658–6662; Takeda K, et al., J. Immunol. 1996; 156: 3366–3373; and Siders W M, et al., J. Immunol. 1998; 160: 5465–33735474).

NK cells respond to and are important in defense against a number of different infectious agents, including viruses, bacteria, protozoa, and parasites (Biron C A., Curr. Opin. Immunol. 1997; 9(1): 24–34; Unanue E R., Curr. Opin. Immunol. 1997. 9: 35–43; Scharton-Kersten T M, and Sher A., Curr. Opin. Immunol. 1997. 9: 44–51; Scharton-Kersten T M, and Sher A., Curr. Opin. Immunol. 1997. 9: 44–51; and Scott P, and Trinchieri G., Curr. Opin. Immunol. 1995. 7: 34–40). There are not many effective drugs for some of the infectious agents, for example, viruses. The emergences of drug resistant variants are one of the most difficult tasks for health care worldwide. NK cells participate in innate immunity and early defense within several hours to days after primary infections, whereas adaptive T and B cell responses develop after more than one week. Virus, such as arenaviruses (Welsh R M., J. Exp. Med. 1978. 148: 163–181), herpes viruses (Ching C, and Lopez C., 1979. Infect. Immun. 26: 49–56), orthomyxoviruses (Santoli D, Trinchieri G, and Koprowski H., 1978. J. Immunol. 121: 532–538), and picornaviruses (Godeny E K, and Gauntt C J., 1986. J. Immunol. 137: 1695–1702) induced interferon $\alpha/\beta$ enhance NK cell-mediated cytotoxicity. NK cells can produce antimicrobial and immunoregulatory cytokines, such as interferon $\gamma$ (Orange J S, and Biron C A., 1996. J. Immunol. 156: 4746–47; and Orange J S, Wang B, Terhorst C, and Biron C A., 1995. J. Exp. Med. 182: 1045–1056). Low NK cell cytotoxic activity was linked with increased sensitivity to severe disseminating herpes infection (Biron C A, Byron K S, and Sullivan J L., 1989. N. Engl. J. Med. 320: 1731–1735; and Joncas J, Monczak Y, Ghibu F, Alfieri C, Bonin A, Ahronheim G, and Rivard G., 1989. J. Med. Virol. 28:110–117). There is also evidence showed that IL-2 increased LAK activity preferentially against HBV transfected HepG2-2215 cells when compared with parental HepG2 cells (Tsang T, Se C J, Yu M, and Tang, S L., 1994. Chung Hwa Yi Hsueh Tsa Chih 74(4):235–237).

SUMMARY OF INVENTION

The present invention involves the preparation and use of a formulation, ST 188L, a Chinese herbal medicine, on preventing and treating cancers and infectious diseases.

One aspect of the invention is to provide for a pharmaceutical composition for preventing and treating cancers comprising a formulation prepared ratably from a group of herbal plants consisting essentially of *Ecchinops grijissii, Cirsium segetum* Bge, *Solanum indicum* Linn, *Lonicerae flos*, and *Zizyphi fructus* in a pharmaceutically acceptable carrier or diluent. The *Ecchinops grijissii, Cirsium segetum* Bge, *Solanum indicum* Linn, *Lonicerae flos*, and *Zizyphi fructus* are prepared in this pharmaceutical composition respectively at a ratio of 5–15:2–6:2–6:1–10:1–5, preferably, at a ratio of 5:2:2:1:1. The formulation can be prepared in many desirable medicine dosage forms such as a tablet, soft gel, granule, powder, liquid, capsule or honey ball.

One more aspect of the invention is to provide for a method of providing therapeutical benefits to a recipient for preventing and treating cancers, which comprises the steps of preparing a pharmaceutical composition selected from extracts of a group of herbal plants consisting essentially of *Ecchinops grijissii, Cirsium segetum* Bge, *Solanum indicum* Linn, *Lonicerae flos*, and *Zizyphi fructus*; formulating said extracts in a pharmaceutically acceptable carrier or diluent in an amount sufficient to provide the intended therapeutical benefits; and administering said pharmaceutical composition to said recipient. The pharmaceutical composition is preferably administered by an oral route in a variety of desirable medicine dosage forms including, but without limitation to, a tablet, soft gel, granule, powder, liquid, capsule or honey ball. The amount of the pharmaceutical composition sufficient to provide the intended benefits is at the range of 0.75 g/Kg/day to 1.5 g/Kg/day.

One more aspect of the invention is to provide for a method and a pharmaceutical composition, that comprises the same ST 188L formulation prepared ratably from *Ecchinops grijissii, Cirsium segetum* Bge, *Solanum indicum* Linn, *Lonicerae flos*, and *Zizyphi fructus* in a pharmaceutically acceptable carrier or diluent at a ratio of 5–15:2–6:2–6:1–10:1–5, for enhancing endogenous immune system of a recipient. Evidence shows that the recipient's endogenous immune system is enhanced due to the increase of natural killer cells and lymphokine activated killer cells.

One additional aspect of the invention is to provide for a pharmaceutical composition and a method of using it for preventing and treating infectious diseases. The pharmaceutical composition comprises a formulation prepared ratably from the group of herbal plants consisting essentially of *Ecchinops grijissii, Cirsium segetum* Bge, *Solanum indicum* Linn, *Lonicerae flos*, and *Zizyphi fructus* in a pharmaceutically acceptable carrier or diluent at a ratio of 5–15:2–6:2–6:1–10:1–5, and, preferably, at 5:2: 2:1:1. This pharmaceutical composition is suitable for preventing and treating infectious diseases caused by an infectious agent is a virus, bacteria, protozoa, or parasite.

Additionally, ST 188L was found to be non-toxic in vitro and was non-toxic in vivo up to 19.8 g/Kg in rats. ST 188L has been demonstrated efficacious in some cancer patients as evident in its ability of inducing NK cell activity and enhancing IL-2 induced lymphokine activated killer cell (LAK) activity in human peripheral blood mononuclear cells in vivo. As such, its anti-cancer activity mechanisms observed clinically were due to its immune modulation activity after metabolic activation in vivo. ST 188L incubated with K562 cells in vitro did not significantly modify K562 cells to become more susceptible to NK cells. In vitro treatment of PBMC with ST 188L somehow decreased its LAK activity. Thus, ST 188L appeared to be activated in vivo to stimulate the activity of NK cells and LAK cells. This was shown by the increases in cytolytic activity of PBMC isolated from volunteers after intake of ST 188L toward K562 and Daudi target cells in a dose dependent manner. Furthermore, intake of ST 188L also potentiated IL-2's activity in a dose dependently. Consequently, the activation of NK and LAK activities by in vivo ST 188L administration can treat and prevent the occurrence, recurrence and metastasis of cancers, since NK and LAK cells are the first line of immune surveillance in vivo against cancers. The activation of NK and LAK activities by ST 188L in vivo may have activity in prevention and treatment of infectious agent, such as virus, bacteria, protozoa, and parasite infections.

DETAILED DESCRIPTION OF THE INVENTION

A. PREPARATION OF ST 188L

EXAMPLE I

Figure 1:
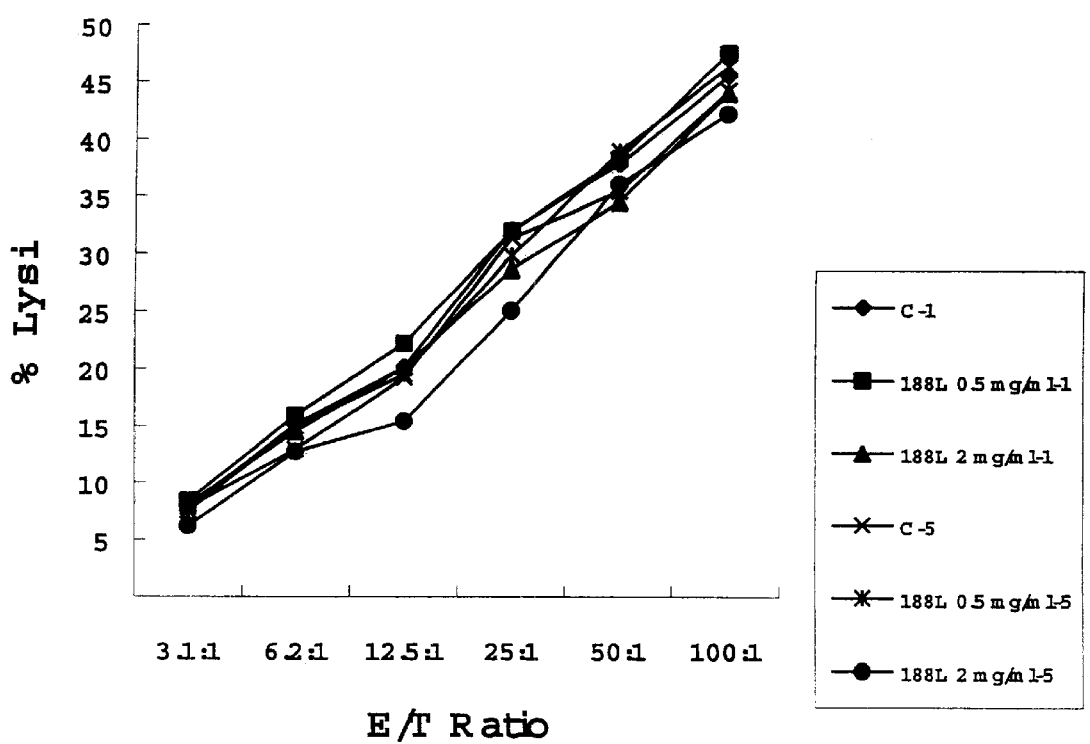
FIG. 1 shows the NK activity of PBMC toward K562 cells treated with various concentrations of ST 188L for 1 or 5 days in vitro.

1). 5 Kg *Ecchinops grijissii*, 2 Kg *Cirsium segetum* Bge, 2 Kg *Solanum indicum* Linn, 1 Kg *Lonicerae flos*, and 1 Kg *Zizyphi fructus* were washed, cut into small pieces and placed in a stainless tank;

2). 78080 ml of water was added into the tank and boiled by high heat. After it was boiling, the heat was turned to low for 1 hour and 40 minutes;

3). The volume of supernatant was about 35600 ml and was collected which was then passed through 80 mesh;

4). 64700 ml of water was added into the precipitate and repeated the boiling procedure as in step 2 one more time;

5). The volume of supernatant was about 23700 ml and was collected which was then passed through 80 mesh;

6). The supernatants of steps 3 and 5 were pooled and mixed;

7). 250 ml of the pooled supernatant was poured and sealed into each can; and

8). The cans with 188L were sterilized by autoclaving at 121° C. for 8 minutes.

EXAMPLE II

The pooled supernatant as described in Example I (with *Ecchinops grijissii, Cirsium segetum* Bge, *Solanum indicum* Linn, *Lonicerae flos*, and *Zizyphi fructus* at the ratio of 8:2:2:2:1) can be lyophilized or spray-dried, and formulated into tablet, soft gel, granulated, powder, and capsulated dosage forms.

EXAMPLE III

The five medicinal herbs (with *Ecchinops grijissii, Cirsium segetum* Bge, *Solanum indicum* Linn, *Lonicerae flos*, and *Zizyphi fructus* at the ratio of 15:6:6:10:5 by dry weight)can be grounded into powder and mixed with honey, and formulated into traditional Chinese medicinal balls.

EXAMPLE IV

The five medicinal herbs (with *Ecchinops grijissii, Cirsium segetum* Bge, *Solanum indicum* Linn, *Lonicerae flos*, and *Zizyphi fructus* at the ratio of 10:3:3:2:2 by dry weight) can be grounded into powder and mixed with lactose, starch, acicel, priomojel, prejel, sodium cross carmellose, hydroxymethylcellulose, hydroxypropylcellulose, PVP, magnesium stereate, and formulated into various western medicine dosage forms.

EXAMPLE V

The five medicinal herbs (with *Ecchinops grijissii, Cirsium segetum* Bge, *Solanum indicum* Linn, *Lonicerae flos*, and *Zizyphi fructus* at the ratio of 5:5:5:3:3 by dry weight) can be grounded and formulated into powder for suspension, oral powder, granule for suspension, tablet, pellet, or flake by traditional Chinese herbal medicine formulation methods.

B. EVIDENCES OF BIOLOGICAL ACTIVITIES (B.1)-In Vitro Cytotoxicity Studies

The in vitro cytotoxicity studies of ST 188L were performed on several cell lines including Nasopharyngeal carcinomasuch as NPC039, NPC076, NPC-bm1, NPC-bm2, CM23, MEWO, Hematopoetic cancersuche as Daudi, HL60, K562, and Neuroblastoma such as Y79. The cell lines were cultured in a culture medium, RPMI1640, which is commercially available from HyClone Lab., Logan, Utah based on the formula disclosed by Moore et al, at Rosewell Park Memorial Institute in 1966., Briefly, RPMI-1640 contains essentially of L-Arginine HCl 200 mg/L, L-Asparagine 50 mg/L, L-Aspartic acid 20 mg/L, L-Cystine 2HCl 65.15 mg/L, L-Glutamic acid 20 mg/L, Glycine 10 mg/L, L-Histidine FB 15 mg/L, L-Hydroxyproline 20 mg/L, L-Isoleucine 50 mg/L, L-Leucine 50 mg/L, L-Lysine HCl 40 mg/L, L-Methionine 15 mg/L, L-Phenylalanine 15 mg/L, L-Proline 20 mg/L, L-Serine 30 mg/L, L-Threonine 20 mg/l, L-Tryptophan 5 mg/L, L-Tyrosine $2Na_2H_2O$ 28.83 mg/L, L-Valine 20 mg/L, $Ca(NO_3)_2$ $4H_2O$ 100 mg/L, KCl 400 mg/L, $MgSO_4$ (anhydrous) 48.84 mg/L, NaCl 6000 mg/L, $Na_2HPO_4$ (anhydrous) 800 mg/L, d-Biotin 0.2 mg/L, D-Ca Pantothenate 0.25 mg/L, Cholinee chloride 3 mg/L, Folic acid 1 mg/L, Myo-Inositol 35 mg/L, Niacinamide 1 mg/L, Pyridoxine HCl 1 mg/L, Riboflavin 0.2 mg/L, Thiamine HCl 1 mg/L, Vitamin $B_{12}$ 0.005 mg/L, D-Glucose 2000 mg/L, Para-aminobenzoic acid 1 mg/L, Glutathione (reduced) 1 mg/L, Phenol red (Sodium) 5.3 mg/L, $NaHCO_3$ 2000 mg/L.), 10% fetal calf serum (FCS) 2 mM Glutamine, 1 mM Na Pyruvate, 100 units/ml Penicillin and 100 ug/ml Streptomycin. ST 188L was lyophilized and weighed. The concentration was 90 mg/ml.

(B. 1.1)-$^3$H-Thymidine Uptake Assay.

Cells ($2\times10^3$/150 ul medium/well) were seeded to 96 well plates and incubated for 48 hours at 37° C. Serial diluted ST 188L (30, 20, 10, 5, 2.5, 1.25 and 0.625 mg/ml in 100 ul medium/well) was added, and plates were incubated for a further of 16 hours. $^3$H-Thymidine (1 uCi/20 ul/well) was added and incubated for 8 hours before harvesting. The acid precipitated $^3$H-Thymidine incorporated DNA was counted by a β counter. Cells without drug and with medium alone were served as controls. Results were shown in Table 1.

TABLE 1

% Inhibition of $^3$H-Thymidine incorporation by ST188L Cell Lines

| Conc. (mg/ml) | HL60 | Y79 | Daudi | K562 | NPC 039 | NPC 076 | NPC -bm1 | NPC -bm2 | CM23 | Mewo |
|---|---|---|---|---|---|---|---|---|---|---|
| 30 | | | | | 0.03 | −0.06 | −0.10 | 0.80 | | |
| 20 | −0.01 | −0.22 | −0.05 | 0.10 | 0.56 | 0.02 | 7.48 | 13.36 | −0.03 | −0.04 |
| 10 | 0.14 | 0.19 | 0.88 | 0.72 | 7.92 | 0.30 | 45.01 | 19.83 | −0.01 | −0.06 |
| 5 | 3.01 | 1.21 | 2.96 | 11.61 | 17.51 | 3.17 | 113.09 | 52.78 | 0.34 | 2.38 |
| 2.5 | 29.16 | 16.99 | 23.73 | 39.67 | 26.43 | 24.39 | 218.67 | 127.13 | 10.86 | 17.23 |
| 1.25 | 63.41 | 42.14 | 56.29 | 48.89 | 31.44 | 50.98 | 244.74 | 149.64 | 39.73 | 34.57 |
| 0.625 | 79.81 | 60.49 | 79.65 | 59.45 | | | | | 67.65 | 54.92 |

Based on Table 1, $IC_{50}$ of ST 188L obtained by $^3$H-Thymidine uptake assay were about 1 mg/ml for most of the cell lines studied. For NPC-bm1 and NPC-bm2, $IC_{50}$ were about 5–10 mg/ml. ST 188L at low concentration showed growth stimulation effect on NPC-bm1 and NPC-bm2 cells.

(B. 1. 2)-Growth Inhibition.

Cells were seeded at $2\times10^5$ per well to 6-well plates in triplicates. Various concentrations of ST 188L as indicated were added. Cells were harvested daily up to day 5. Total cell number and cell viability were determined by Trypan blue dye exclusion, and were observed and counted by hemocytometer under inverted phase microscope. The results were shown in Tables 2 to 6.

TABLE 2

Growth inhibition of NPC-bm1 by ST 188L

| | NPC-bm1 | | | | | | | |
|---|---|---|---|---|---|---|---|---|
| | 0 mg/ml | | 2 mg/ml | | 5 mg/ml | | 10 mg/ml | |
| Day | Cell # ($\times 10^5$) | % of control | Cell # ($\times 10^5$) | % of control | Cell # ($\times 10^5$) | % of control | Cell # ($\times 10^5$) | % of control |
| 0 | 2.0 | 98.2 | 2.0 | 98.2 | 2.0 | 98.2 | 2.0 | 98.2 |
| 1 | 5.8 | 97.1 | 5.9 | 97.8 | 4.5 | 97.8 | 2.2 | 86.9 |
| 2 | 13.0 | 99.0 | 13.0 | 96.6 | 8.0 | 97.2 | 2.0 | 79.5 |
| 3 | 16.0 | 94.2 | 14.0 | 96.6 | 12.0 | 94.2 | 1.7 | 76.2 |
| 4 | 15.0 | 92.3 | 13.0 | 93.0 | 15.0 | 92.5 | 0.6 | 67.0 |
| 5 | 14.0 | 86.2 | 10.0 | 91.4 | 12.0 | 46.0 | 0.5 | 18.2 |

TABLE 3

Growth inhibition of NPC-bm2 by ST 188L

| | NPC-bm2 | | | | | | | |
|---|---|---|---|---|---|---|---|---|
| | 0 mg/ml | | 2 mg/ml | | 5 mg/ml | | 10 mg/ml | |
| Day | Cell # ($\times 10^5$) | % of control | Cell # ($\times 10^5$) | % of control | Cell # ($\times 10^5$) | % of control | Cell # ($\times 10^5$) | % of control |
| 0 | 2.0 | 97.8 | 2.0 | 97.8 | 2.0 | 97.8 | 2.0 | 97.8 |
| 1 | 4.3 | 96.6 | 3.6 | 95.5 | 2.6 | 94.3 | 32.0 | 89.6 |
| 2 | 7.9 | 96.4 | 7.3 | 95.4 | 5.6 | 97.1 | 1.5 | 89.6 |
| 3 | 13.0 | 97.0 | 12.0 | 94.9 | 8.6 | 96.8 | 1.3 | 81.0 |
| 4 | 13.0 | 96.7 | 13.0 | 90.7 | 9.9 | 92.7 | 1.0 | 75.7 |
| 5 | 12.0 | 92.3 | 12.0 | 84.8 | 8.1 | 83.9 | 0.9 | 47.2 |

TABLE 4

Growth inhibition of Daudi by ST 188L

| | Daudi | | | | | | | |
|---|---|---|---|---|---|---|---|---|
| | 0 mg/ml | | 2 mg/ml | | 5 mg/ml | | 10 mg/ml | |
| Day | Cell # ($\times 10^5$) | % of control | Cell # ($\times 10^5$) | % of control | Cell # ($\times 10^5$) | % of control | Cell # ($\times 10^5$) | % of control |
| 0 | 2.0 | 93.5 | 2.0 | 93.5 | 2.0 | 93.5 | 2.0 | 93.5 |
| 1 | 2.7 | 92.6 | 1.7 | 69.9 | 1.0 | 44.2 | 0.5 | 28.7 |
| 2 | 3.8 | 86.1 | 0.6 | 32.1 | 0 | 0 | 0 | 0 |
| 3 | 3.9 | 88.2 | 1.9 | 10.0 | 0 | 0 | 0 | 0 |
| 4 | 3.6 | 86.1 | 0 | 0 | 0 | 0 | 0 | 0 |
| 5 | 2.7 | 75.0 | 0 | 0 | 0 | 0 | 0 | 0 |

TABLE 5

Growth inhibition of K562 by ST 188L

| | K562 | | | | | | | |
|---|---|---|---|---|---|---|---|---|
| | 0 mg/ml | | 2 mg/ml | | 5 mg/ml | | 10 mg/ml | |
| Day | Cell # ($\times 10^5$) | % of control | Cell # ($\times 10^5$) | % of control | Cell # ($\times 10^5$) | % of control | Cell # ($\times 10^5$) | % of control |
| 0 | 2.0 | 98.7 | 2.0 | 98.7 | 2.0 | 98.7 | 2.0 | 98.7 |
| 1 | 4.9 | 98.3 | 3.6 | 96.0 | 1.8 | 80.0 | 0.4 | 18.2 |
| 2 | 12.8 | 97.9 | 6.3 | 95.9 | 2.8 | 70.1 | 0 | 0 |
| 3 | 21.8 | 98.2 | 10.1 | 95.7 | 2.6 | 70.8 | 0 | 0 |
| 4 | 23.7 | 93.6 | 14.2 | 93.5 | 2.1 | 60.6 | 0 | 0 |
| 5 | 20.0 | 88.7 | 12.6 | 89.4 | 1.8 | 54.4 | 0 | 0 |

TABLE 6

Growth inhibition of Y79 by ST 188L

| | Y79 | | | | | | | |
|---|---|---|---|---|---|---|---|---|
| | 0 mg/ml | | 2 mg/ml | | 5 mg/ml | | 10 mg/ml | |
| Day | Cell # ($\times 10^5$) | % of control | Cell # ($\times 10^5$) | % of control | Cell # ($\times 10^5$) | % of control | Cell # ($\times 10^5$) | % of control |
| 0 | 2.0 | 98.3 | 2.0 | 98.3 | 2.0 | 98.3 | 2.0 | 98.3 |
| 1 | 3.4 | 95.8 | 3.0 | 89.4 | 1.3 | 59.3 | 0 | 0 |
| 2 | 6.7 | 94.4 | 4.1 | 87.9 | 0.1 | 5.3 | 0 | 0 |
| 3 | 15.4 | 95.8 | 5.2 | 87.0 | 0 | 0 | 0 | 0 |
| 4 | 39.5 | 97.3 | 4.9 | 82.5 | 0 | 0 | 0 | 0 |
| 5 | 34.7 | 92.8 | 3.8 | 76.8 | 0 | 0 | 0 | 0 |

The growth inhibition studies showed that $IC_{50}$ of ST 188L were about 5 to 10 mg/ml on day 5 in NPC-bm1 and NPC-bm-2 cells, which were not very toxic. However, Daudi cell was much more sensitive to ST 188L, on day 2, the $IC_{50}$ was 1 to 2 mg/ml. The $IC_{50}$ of K562 cells on day 5 was about 5 mg/ml. The $IC_{50}$ of Y79 cells on day 5 was about 2 to 5 mg/ml. It shows that ST 188L was not very toxic in inhibiting Thymidine incorporation and growth of tumor cell lines studied.

(B. 2)-In Vivo Acute Toxicity Study in Rats.

Sprague-Dawley Rats at 6 to 7 weeks of age, 6 males and 6 females in each group, were used for the in vivo acute toxicity study. ST 188L was given by oral gavage at 0, 6.6, 13.2, or 19.8 g/Kg equally divided into two doses in two hours apart. The rats were observed and documented for mortality and clinical sign twice daily for 14 days. Body weights were measured prior to dosing and weekly for two weeks. The surviving rats were necropsied for any organ abnormality. The results of mean body weight change and weight gain were shown in Table 7.

(B. 3)-In Vitro Immune Modulation Studies.

The in vitro immune modulation studies were evaluated on target cells, such as K562, Daudi, HepG2 or HepG2-2215 cell lines which were cultured in the same medium described in the in vitro cytotoxicity studies of B. 1 above. (hereinafter referred to as "Complete Medium", "C-medium") under humidified atmosphere with 5% $CO_2$ at 37° C. The target cells were labeled with 100 uCi $Cr^{51}$ at the concentration of $4 \times 10^6$ cells/ml for 90 minutes at 37° C. The labeled cells were washed twice with phosphate buffered saline (PBS) and diluted to $1 \times 10^5$ cells /ml with C-medium.

Peripheral Blood Mononuclear Cells (PBMC).

Blood was freshly drawn by veni-puncture, diluted 2 folds with PBS+2% FCS, and PBMC was isolated with Ficoll Paque (4° C.) at the ratio of diluted blood:Ficoll Paque=4:3 by centrifugation at 800×g at 16–18° C. for 40 minutes. The cells at the inter-phase between plasma and Ficoll Paque were collected and washed with PBS+2% FCS at 37° C. for 10–15 minutes, and one more time with PBS+2% FCS at room temperature. The cells were counted and diluted to $3.33 \times 10^6$ cells/ml in C-medium as the effector cells.

TABLE 7

Acute oral toxicity study of ST188L in SD rats - mean body weights and weight gains (Mean ± SD, N = 6)

| Sex | Dose (g/Kg) | Mean body weights (g) | | | Weight gains (g) |
|---|---|---|---|---|---|
| | | Initial (Day 1) | (Day 8) nal | (Day 15) Day 15 | |
| Male | 0 | 210.0 ± 12.2 | 314.8 ± 19.3 | 381.2 ± 22.8 | 170.7 ± 11.1 |
| | 6.6 | 218.5 ± 12.4 | 318.8 ± 20.7 | 389.0 ± 28.7 | 170.5 ± 17.0 |
| | 13.2 | 216.0 ± 16.4 | 315.2 ± 22.6 | 383.2 ± 28.6 | 167.2 ± 15.6 |
| | 19.8 | 216.5 ± 9.6 | 311.0 ± 16.1 | 376.0 ± 17.1 | 159.5 ± 11.3 |
| Female | 0 | 170.3 ± 8.3 | 222.7 ± 11.7 | 244.2 ± 15.4 | 73.8 ± 13.8 |
| | 6.6 | 174.7 ± 8.1 | 225.2 ± 10.4 | 241.5 ± 8.0 | 66.8 ± 8.4 |
| | 13.2 | 174.7 ± 10.2 | 216.5 ± 19.0 | 236.2 ± 23.2 | 61.5 ± 13.8 |
| | 19.8 | 174.0 ± 7.5 | 223.7 ± 7.2 | 243.5 ± 9.6 | 69.5 ± 11.2 |

The in vivo acute toxicity study showed that there was no mortality observed in control and ST 188L treated rats during the study. In a few rats at 19.8 g/Kg, there were transient sign of soft feces within 4 hours after dosing, and all rats recovered within 2 days. All rats appeared essentially normal for the remainder of the 14-day observation period. There were no differences in mean body weights and body weight gains between the control and ST 188L treated rats. Necropsy of all rats at the termination did not reveal any gross lesions. ST 188L at 19.8 g/Kg only caused transient soft feces. There was no other toxic effect observed at this high dose that was 13.2 to 26.4 folds of recommended dose for human use.

$Cr^{51}$ Release Cytotoxicity Assay.

150 ul of 2 fold serially diluted PBMC, C-mediun alone (spontaneous release) or C-medium+2% SDS (maximal release) were pipetted into U-bottom 96-well plate in triplicates. 50 ul of $Cr^{51}$ labeled target cells, such as K562, Daudi, HepG2 or HepG2-2215 cells was pipetted into each well. The cells were incubated under humidified atmosphere with 5% $CO_2$ at 37° C. for 4 hours. At the end of incubation, the plate was centrifuged at 800×g at 20° C. for 10 minutes. 40 ul of the supernatant of each well was transferred to LumaPlate-96. The plate was air-dried overnight and covered with adhesive film before counting by a gamma counter, Cobra 5000 (Parkard, Doowners Groove, Ill.).

The results were expressed as % specific $Cr^{51}$ release and calculated using the following formula:

% Lysis=(Experimental release−Spontaneous release)/(Maximal release−Spontaneous release)×100%

Results were converted to lytic unit (LU) per $10^7$ cells, with one unit defined as the number of effector cells required to produce 30% lysis of $5\times10^3$ target cells during the incubation period. The NK activity was assayed by standard 4 hours $Cr^{51}$ release cytotoxicity assay. The LAK activity was assayed by standard 4 hours $Cr^{51}$ release cytotoxicity assay after incubation with substance of interest or Interleukine-2 (IL-2, R&D Systems Inc., Minneapolis, Minn.) for 3 days in vitro.

(B. 3. 1)-ST 188 L Treatment on K562 Cells.

(B. 3. 1. 1)-K562 cells were treated with ST 188 L at 0.5, or 2 mg/ml for 1, or 5 days.

After washing with PBS, the counted cells were labeled with $Cr^{51}$, and the NK activity of PBMC was detected by $Cr^{51}$ release cytotoxicity assay. The results were shown in FIG. 1 wherein C-1 represents control treatment for 1 day; 188L 0.5 mg/ml-1 represents 0.5 mg/ml 188L treatment for 1 day; 188L 2 mg/ml-1 represents 2 mg/ml 188L treatment for 1 day; C-5 represents control treatment for 5 days; 188L 0.5 mg/ml-5 represents 0.5 mg/ml 188L treatment for 5 days; and 188L 2 mg/ml-5 represents 2 mg/ml 188L treatment for 5 days. The lytic units were as follow in Table 8.

TABLE 8

Lytic units of PBMC on K562 cells treated with ST 188L in vitro

| Treatment | Lytic Unit | % of Control |
| --- | --- | --- |
| Control | 82.18 | 100 |
| 188L, 0.5 mg/ml, 1 day | 100.52 | 122 |
| 188L, 2.0 mg/ml, 1 day | 64.29 | 78 |
| 188L, 0.5 mg/ml, 5 days | 91.29 | 111 |
| 188L, 2.0 mg/ml, 5 days | 85.58 | 104 |

As shown in Table 8, K562 cells incubated with ST 188L at 0.5 mg/ml for 1 day increased slightly the lytic activity of NK cells. At 2 mg/ml, there was some inhibition. After 5 days of incubation, there was less stimulation at 0.5 mg/ml, and less inhibition at 2 mg/ml.

(B. 3. 1. 2)-K562 cells were treated with ST 188 L at 0.02, 0.1, 0.5, or 2.5 mg/ml for 1

Figure 2:
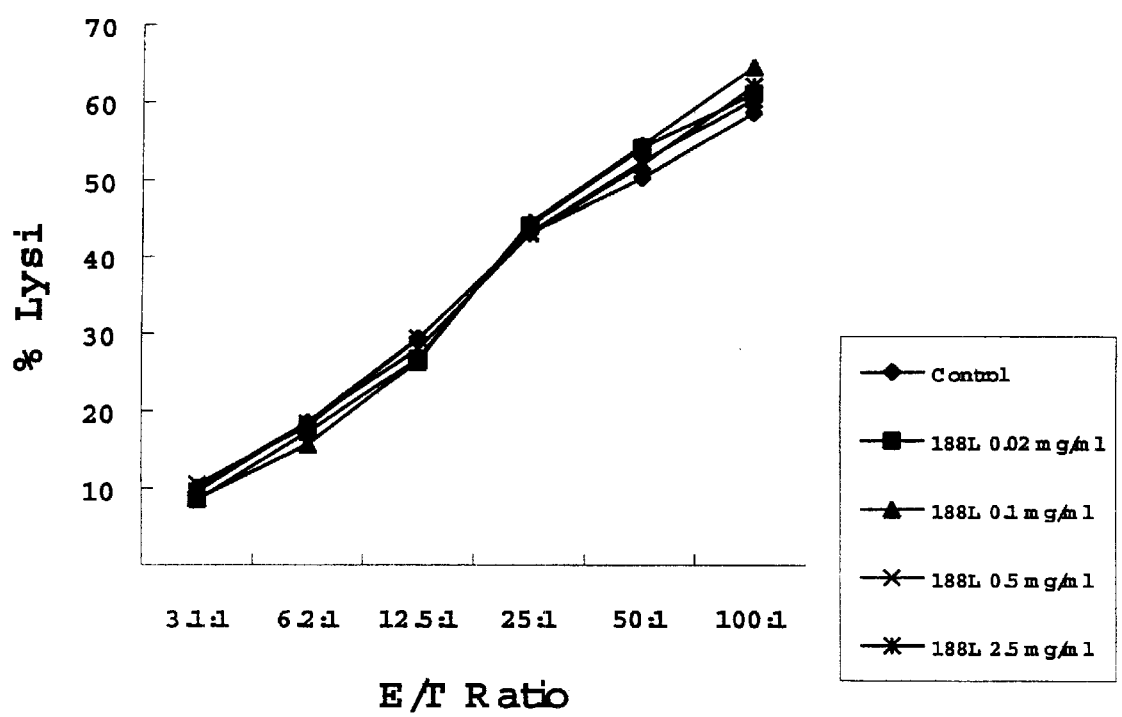
FIG. 2 shows the NK activity of PBMC toward K562 cells treated with various concentrations of ST 188L for 24 hours in vitro.

After washing with PBS, the counted cells were labeled with $Cr^{51}$, and NK activity of PBMC was detected by $Cr^{51}$ release cytotoxicity assay. The results were shown in FIG. 2. The lytic units were as follow in Table 9, which showed that there was no significant difference for NK activity towards K562 cells treated with various concentrations of ST 188L for 24 hours. It appears that ST 188L did not have any significant effect on opsonization of K562 cells.

TABLE 9

Lytic units of PBMC on K562 cells treated with ST 188L in vitro

| Treatment | Lytic Unit | % Change |
| --- | --- | --- |
| Control | 151.57 | 100 |
| 188L, 0.02 mg/ml, 1 day | 146.81 | 97 |
| 188L, 0.1 mg/ml, 1 day | 139.96 | 92 |
| 188L, 0.5 mg/ml, 1 day | 151.16 | 100 |
| 188L, 2.5 mg/ml, 1 day | 144.78 | 104 |

(B. 3. 2)-In Vitro ST 188 L Treatment on PBMC.

Figure 3:
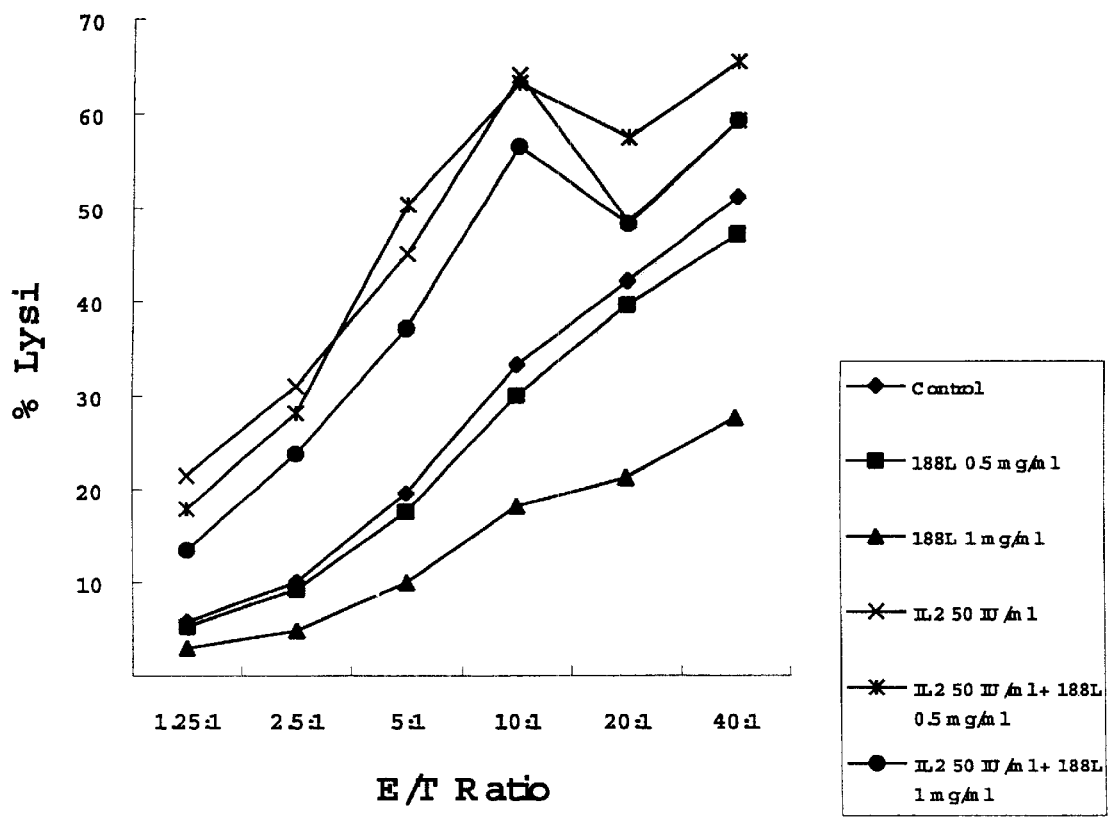
FIG. 3 shows the LAK activity of PBMC toward K562 cells where PBMC were treated with IL-2 (50 IU/ml) or ST 188L (0.5 or 2 mg/ml) or the combination of IL-2 and ST 188L for 5 days in vitro.

Treatment of PBMC with 188L or IL-2 in vitro was conducted. $3.33\times10^6$ PBMC/ml were treated with ST 188L (0.5 or 1.0 mg/ml) or IL-2 (50 IU/ml) or combination of 50 IU/ml IL-2 with ST 188L (0.5 or 1.0 mg/ml) for 5 days. At the end of incubation, the cells were washed with PBS+2% FCS, and $Cr^{51}$ release cytotoxicity assay was performed with $Cr^{51}$ labeled K562 cells as target. The results were shown in FIG. 3. The lytic units were as follow in Table 10.

TABLE 10

Lytic units of PBMC treated with ST 188L in vitro on K562 cells

| Treatment | Lytic Unit | % of Control |
| --- | --- | --- |
| Control | 361.31 | 100 |
| 188L, 0.5 mg/ml, 5 days | 313.00 | 97 |
| 188L, 1.0 mg/ml, 5 days | 150.21 | 42 |
| IL-2, 50 IU/ml, 5 days | 1417.02 | 392 |
| IL-2, 50 IU/ml + 188L, 0.5 mg/ml, 5 days | 1411.20 | 391 |
| IL-2, 50 IU/ml + 188L, 1.0 mg/ml, 5 days | 971.48 | 269 |

The results showed that PBMC, incubated with ST 188L in vitro at the concentrations that were nontoxic to PBMC (data not shown) for 5 days, decreased their cytotoxic activity to K562 cells in a dose depedent manner. However, 0.5 mg/ml ST 188L did not affect the lytic activity enhanced by IL-2. But, at 1 mg/ml, ST 188L significantly decreased the lytic activity of PBMC enhanced by IL-2. It was unclear, however, how ST 188L antagonized the activity of IL-2 in vitro. It is apparent that in vitro treatment of PBMC with ST 188L decreased their NK and LAK activities toward K562 cells.

(B. 4)-Ex Vivo Treatment of ST 188 L on Healthy Volunteers.

(B. 4. 1)-NK Activity.

Figure 4:
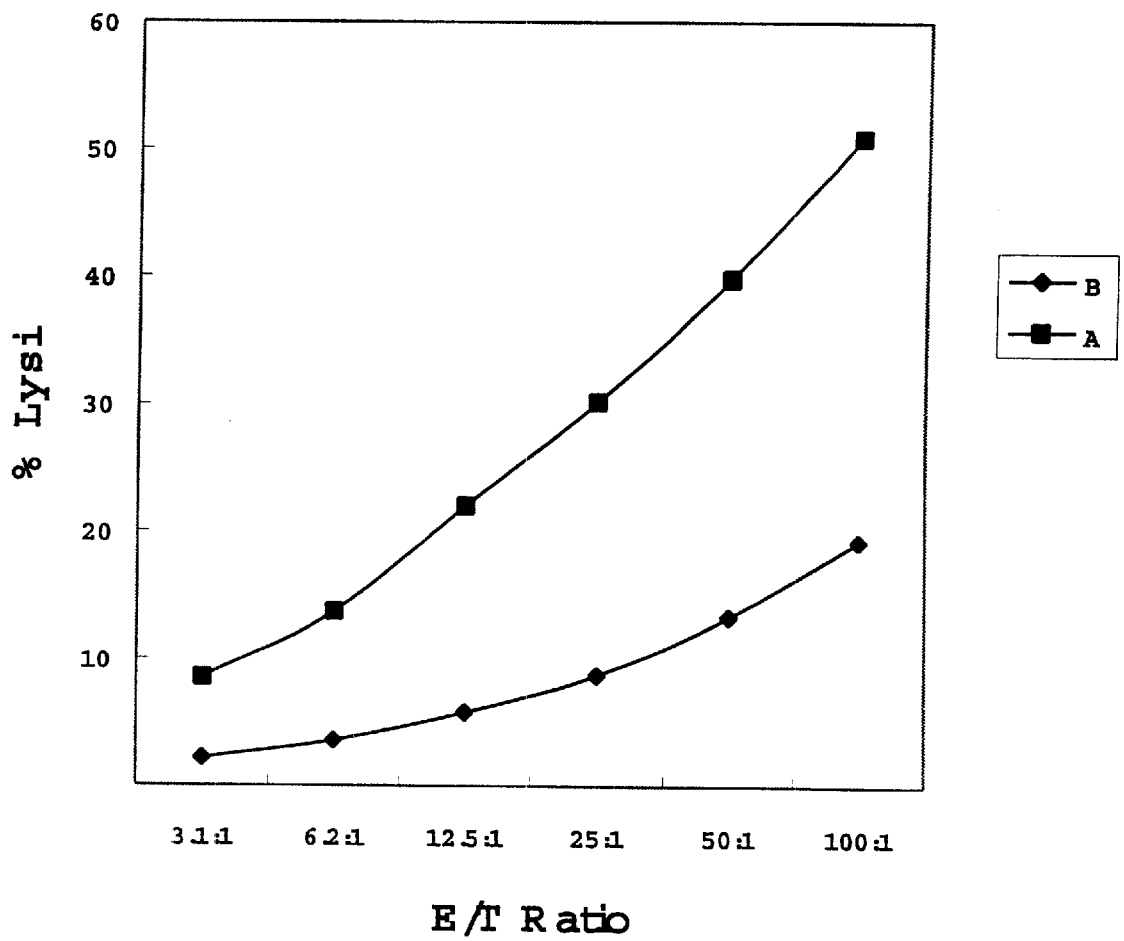
FIG. 4 shows the NK activity of PBMC toward K562 cells where a volunteer was treated with 0.75 g/Kg ST 188L orally for 7 days.

Five healthy male volunteers' PBMC were collected, isolated, and frozen at −70° C. on day 1. Each one of them started to intake ST 188L at the dosage of 0.75 g/Kg/day, BID, orally for 7 days. On day 8, their PBMC were collected and isolated. NK activity was performed with $Cr^{51}$ release cytotoxicity assay by using $Cr^{51}$ labeled K562 cells as target. The result was shown in FIG. 4 represented by volunteer A wherein B represents PBMC isolated before in vivo treatment of ST 188L at 0.75 g/Kg for 7 days; and A represents PBMC isolated after in vivo treatment of ST 188L at 0.75 g/Kg for 7 days. The lytic units were as follow in Table 11.

TABLE 11

Lytic units of PBMC treated with ST 188L in vivo on K562 cells

| Volunteer | Age | BW (Kg) | Treatment | Lytic Unit | % of Control |
| --- | --- | --- | --- | --- | --- |
| A | 35 | 60 | Before 188L intake | 43.06 | 100 |
|   |   |   | After 188L intake | 127.75 | 297 |
| B | 44 | 76 | Before 188L intake | 16.64 | 100 |
|   |   |   | After 188L intake | 47.54 | 286 |
| C | 44 | 44 | Before 188L intake | 14.62 | 100 |
|   |   |   | After 188L intake | 50.11 | 343 |
| D | 42 | 69 | Before 188L intake | 21.69 | 100 |
|   |   |   | After 188L intake | 121.25 | 559 |
| E | 42 | 74 | Before 188L intake | 16.23 | 100 |
|   |   |   | After 188L intake | 41.21 | 254 |

The results showed that all five volunteers showed increases in NK activity after intake of ST 188L at 0.75 g/Kg/day for 7 days. The increases ranged from 154 % to 459 %. Volunteer A, B, C, and E responded to 188L similarly, while volunteer D showed a very significant increase. The result may be due to that volunteer D had been ingesting ST 188L from time to time two months before the experiment. There may be some kind of memory cells existed.

(B. 4. 2)-NK Activity.

Figure 5:
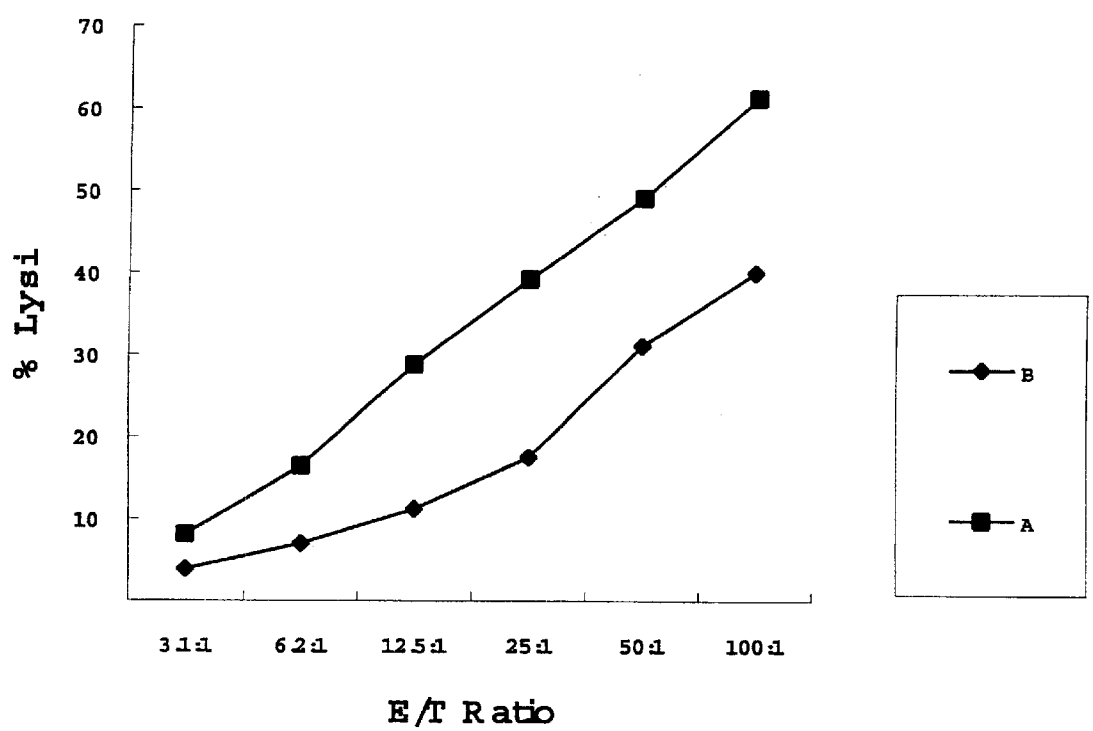
FIG. 5 shows the NK activity of PBMC of volunteer A toward K562 cells where PBMC were isolated from volunteer A before and after treated with 0.75 g/Kg ST 188L orally for 7 days.

Another set of ten healthy volunteers' PBMC were collected, isolated, and frozen at −70° C. on day 1. Each one of them started to intake ST 188L at the dosage of 0.75 g/Kg/day, BID, orally for 7 days. On day 8, their PBMC were collected and isolated. NK activity was performed with $Cr^{51}$ release cytotoxicity assay by using $Cr^{51}$ labeled K562 cells as target. The results were shown in FIG. 5 represented by one volunteer wherein B represents PBMC isolated before in vivo treatment of ST 188L; and A represents PBMC isolated after in vivo treatment of ST 188L. The lytic units were as follow in Table 12.

TABLE 12

Lytic units of PBMC treated with ST 188L in vivo on K562 Cells

| Volunteer | Sex | Age | BW (Kg) | Treatment | Lytic Unit | % of Control |
|---|---|---|---|---|---|---|
| A | M | 41 | 76 | Before ST 188L intake | 25.72 | 100 |
|   |   |   |    | After ST 188L intake | 195.47 | 760 |
| B | M | 34 | 70 | Before ST 188L intake | 11.63 | 100 |
|   |   |   |    | After ST 188L intake | 47.59 | 409 |
| C | M | 44 | 71 | Before ST 188L intake | 2.34 | 100 |
|   |   |   |    | After ST 188L intake | 74.67 | 3191 |
| D | M | 45 | 45 | Before ST 188L intake | 11.50 | 100 |
|   |   |   |    | After ST 188L intake | 33.98 | 295 |
| E | M | 37 | 58 | Before ST 188L intake | 9.75 | 100 |
|   |   |   |    | After ST 188L intake | 50.61 | 519 |
| F | M | 41 | 75 | Before ST 188L intake | 5.38 | 100 |
|   |   |   |    | After ST 188L intake | 20.03 | 372 |
| G | F | 32 | 48 | Before ST 188L intake | 9.26 | 100 |
|   |   |   |    | After ST 188L intake | 26.75 | 289 |
| H | F | 37 | 58 | Before ST 188L intake | * | ** |
|   |   |   |    | After ST 188L intake | 110.71 | ** |
| I | F | 42 | 47 | Before ST 188L intake | 47.22 | 100 |
|   |   |   |    | After ST 188L intake | 645.10 | 1366 |
| J | F | 35 | 49 | Before ST 188L intake | 12.45 | 100 |
|   |   |   |    | After ST 188L intake | 50.83 | 408 |

*Undetectable,
**Unable to calculate.

The results from the second set of ten volunteers (6 males and 4 females) showed significant increases in NK activity after intake of ST 188L at 0.75 g/Kg/day for 7 days. The increases ranged from about 3 to 10 folds.

(B. 4. 3)-LAK Activity.

Figure 6:
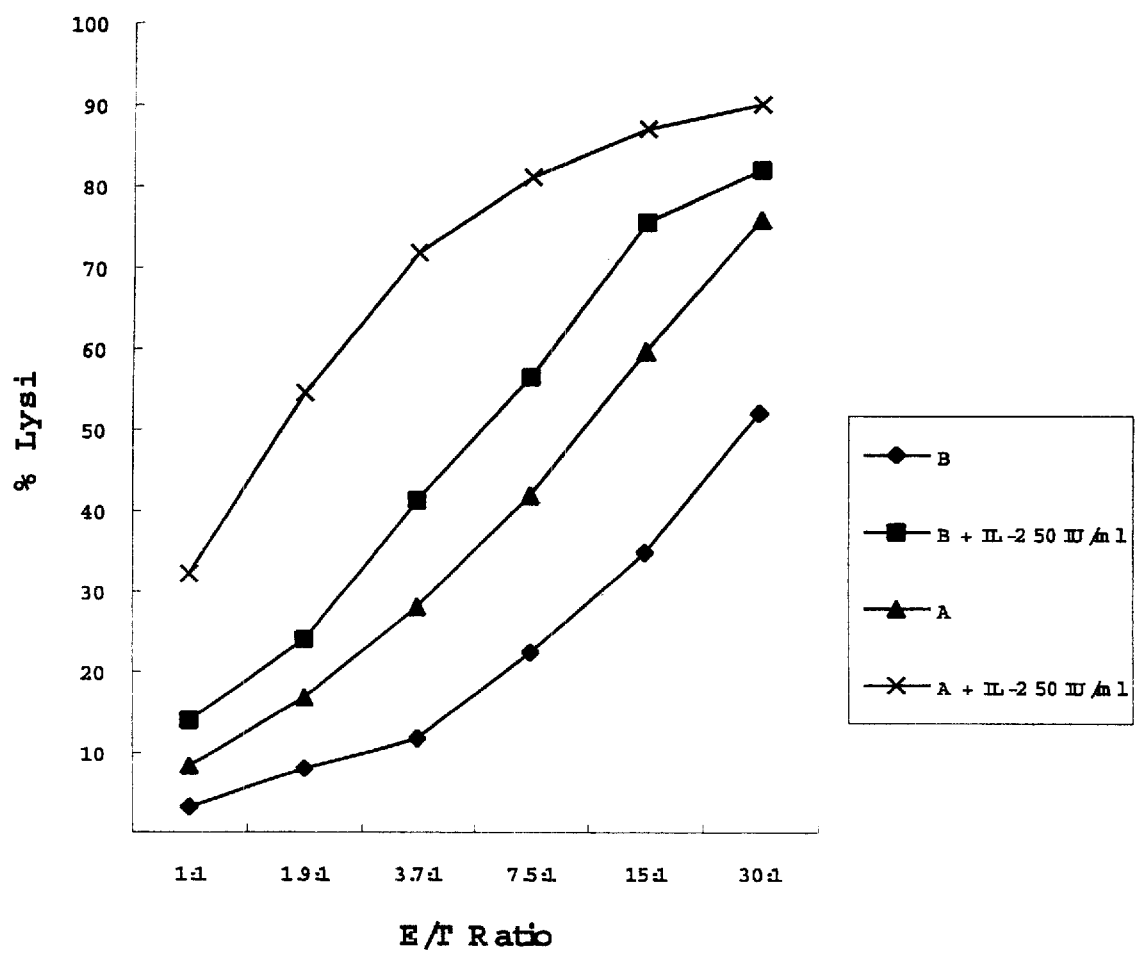
FIG. 6 shows the LAK activity of PBMC of volunteer A toward K562 cells where PBMC were isolated from volunteer A before and after oral administration of ST 188L at 0.75 g/Kg for 7 days.

One healthy male volunteer's PBMC was collected, isolated and frozen at −70° C. on day 1. He started to intake ST 188L at the dosage of 0.75 g/Kg/day, BID, orally for 7 days. On day 8, his PBMC was collected and isolated. LAK activity was performed with $Cr^{51}$ release cytotoxicity assay by using $Cr^{51}$ labeled K562 cells as target. IL-2 at 50 IU/ml was added in vitro for 3 days. The results were shown in FIG. 6 wherein the symbols indicate each of the following treatment groups: B: PBMC isolated before in vivo treatment of ST 188L; B+IL-2 50 IU/ml: PBMC isolated before in vivo treatment of ST 188L for 7 days+IL-2 (50 IU/ml) in vitro treatment for 3 days; A: PBMC isolated after in vivo treatment of ST 188L; and A+IL-2 50 IU/ml: PBMC isolated after in vivo treatment of ST 188L for 7 days+IL-2 (50 IU/ml) in vitro treatment for 3 days. The lytic units were as follow in Table 13.

TABLE 13

Lytic units of PBMC treated with ST 188L in vivo on K562 cells

| Treatment | Lytic Unit | % of Control |
|---|---|---|
| Before ST 188L intake in vivo | | |
| Control | 48.58 | 100 |
| IL-2, 50 IU/ml | 337.88 | 696 |
| After ST 188L intake in vivo | | |
| Control | 198.25 | 408 |
| IL-2, 50 IU/ml | 593.51 | 1222 |

Comparing lytic activity of control before ST 188L intake with after ST 188L intake, LU significantly increased from 48.58 to 198.25. The NK killing activity of PBMC increased 4 times. ST 188L in vivo somehow was activated to become immune-stimulatory. In vivo treatment of ST 188L also potentiated IL-2's activity (LU increased from 337.88 to 593.51).

(B. 4. 4)-NK and LAK Activity.

Two healthy male volunteers' PBMC were collected, isolated, and frozen at −70° C. on day 1. Each one of them started to intake ST 188L at the dosage of 0.75 g/Kg/day, BID, orally for 7 days. On day 8, their PBMC were collected and isolated. NK and LAK activity was performed with $Cr^{51}$ release cytotoxicity assay by using $Cr^{51}$ labeled K562 cells as target. IL-2 at 50 IU/ml was added in vitro for 3 days. The lytic units were as follow in Table 14.

TABLE 14

Lytic units of PBMC treated with ST 188L in vivo on K562 cells

| Volunteer | Age | B.W. (Kg) | Treatment | Lytic Unit | % of Control |
|---|---|---|---|---|---|
| A | 35 | 60 | Before ST 188L intake | | |
|   |    |    | Control | 182.33 | 100 |
|   |    |    | IL-2 (50 IU/ml) | 757.27 | 415 |
|   |    |    | After ST 188L intake | | |
|   |    |    | Control | 448.89 | 246 |
|   |    |    | IL-2 (50 IU/ml) | 2182.93 | 1197 |
| B | 42 | 69 | Before ST 188L intake | | |
|   |    |    | Control | 16.42 | 100 |
|   |    |    | IL-2 (50 IU/ml) | 445.91 | 2716 |
|   |    |    | After ST 188L intake | | |
|   |    |    | Control | 56.11 | 342 |
|   |    |    | IL-2 (50 IU/ml) | 666.64 | 4065 |

The results showed that Volunteer A and B again were confirmed of their high cytotoxic activity toward K562 cells after intake of ST 188L at 0.75 g/Kg/day. Orally administered ST 188L was activated in vivo, and the activated component(s) of the orally administered ST 188L somehow activated NK activity. LAK activity of PBMC by in vitro incubation with IL-2 (50 IU/ml) was significantly potentiated by the in vivo activated ST 188L component(s).

(B. 4. 5)-Dose Responsiveness of NK and LAK Activities by Orally Administered ST 188L.

Health male volunteer's PBMC were collected, isolated, and frozen at −70° C. on day 1. The volunteer started to intake ST 188L at the dosage of 0.75 g/Kg/day, BID, orally for 7 days. On day 8, his PBMC were collected, isolated and frozen at −70° C. On day 8, he continued to intake ST 188L at the dosage of 1.5 g/Kg/day, BID, orally for 7 days. On day 15, his PBMC were collected, isolated, and frozen at −70°

Figure 7:
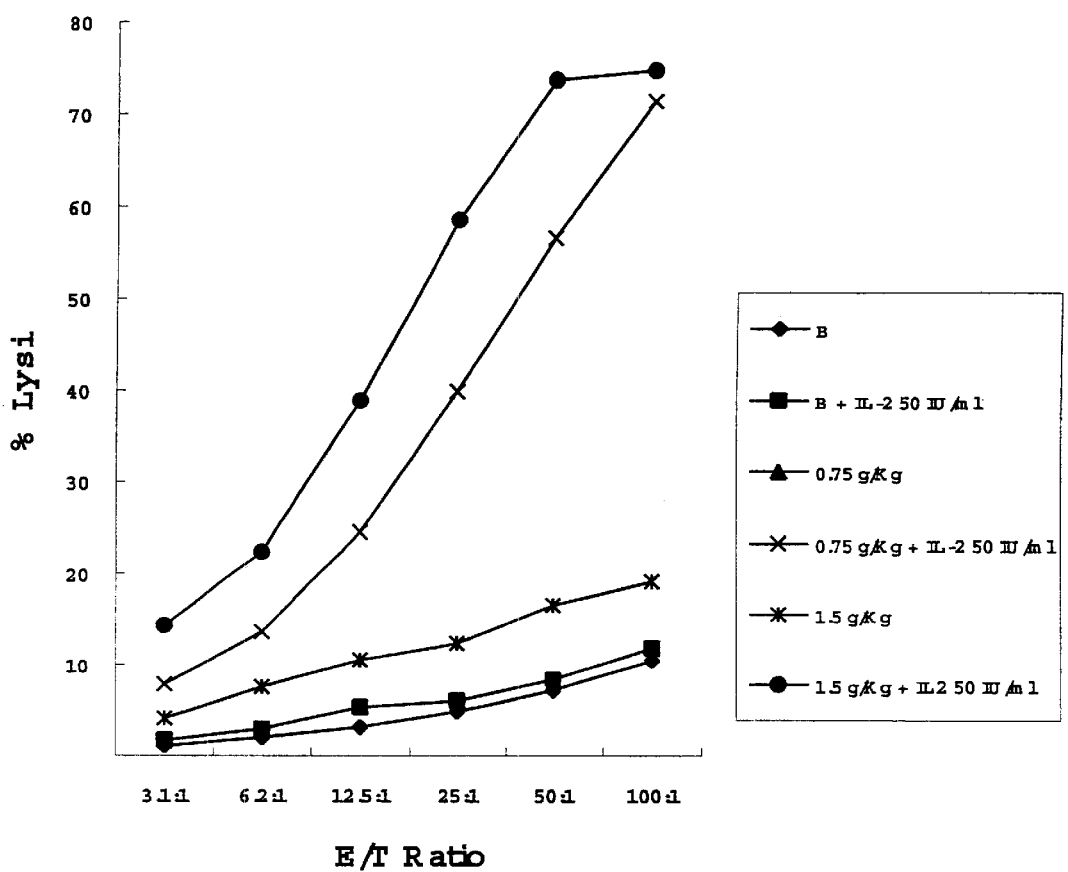
FIG. 7 shows the LAK activity of PBMC toward K562 cells where PBMC were isolated from volunteer treated with 0.75 g/Kg ST 188L orally for 7 days, and from the same volunteer treated with 1.5 g/Kg ST 188L orally for a further of 7 days.

C. NK and LAK activities were performed with Cr$^{51}$ release cytotoxicity assay by using Cr$^{51}$ labeled K562 cells as target, and IL-2 (50 IU/ml) was added in vitro for 3 days. The results were shown in FIG. 7 wherein the symbols indicate each of the following treatment groups: B: PBMC isolated before in vivo treatment of ST 188L; B+IL-2 50 IU/ml: PBMC isolated before in vivo treatment of ST 188L+IL-2 (50 IU/ml) in vitro treatment for 3 days; 0.75 g/Kg: PBMC isolated after in vivo treatment of 0.75 g/Kg ST 188L for 7 days; 0.75 g/Kg+IL-2 50 IU/ml: PBMC isolated after in vivo treatment of 0.75g/Kg ST 188L for 7 days+IL-2 (50 IU/ml) in vitro treatment for 3 days; 1.5 g/Kg: PBMC isolated after in vivo treatment of 1.5 g/Kg ST 188L for 7 days; and 1.5 g/Kg+IL-2 50 IU/ml: PBMC isolated after in vivo treatment of 1.5g/Kg ST 188L for 7 days+IL-2 (50 IU/ml) in vitro treatment for 3 days The lytic units were as follow in Table 15.

TABLE 15

Lytic units of PBMC treated with ST 188L in vivo on K562 cells

| In vivo treatment | In vitro treatment | LU | % of control |
|---|---|---|---|
| | | NK activity | |
| Control | Control | 5.33 | 100 |
| ST 188L 0.75 g/Kg/day, 7days | | 4.98 | 93 |
| ST 188L 1.5 g/Kg/day, 7days | | 15.33 | 288 |
| | | LAK activity | Control |
| | Control | 49.58 | 100 |
| | +IL-2 (50 IU/ml) | 307.29 | 620 |
| ST 188L 0.75 g/Kg/day, 7 days | Control | 70.67 | 143 |
| | +IL-2 (50 IU/ml) | 319.51 | 644 |
| ST 188L 1.5 g/Kg/day, 7 days | Control | 193.99 | 391 |
| | +IL-2 (50 IU/ml) | 781.16 | 1575 |

The results from the volunteer showed a dose dependent increases in cytotoxic activity toward K562 cells after oral intake of ST 188L. Orally administered ST 188L was activated in vivo, and the activated component(s) somehow activated NK activity. LAK activity of PBMC by in vitro incubation with IL-2 (50 IU/ml) was significantly potentiated by the in vivo activated ST 188L in a dose dependent manner.

(B. 4. 6)-Dose Responsiveness of LAK Activity by Orally Administered ST 188L with In Vitro Added IL-2.

Figure 8:
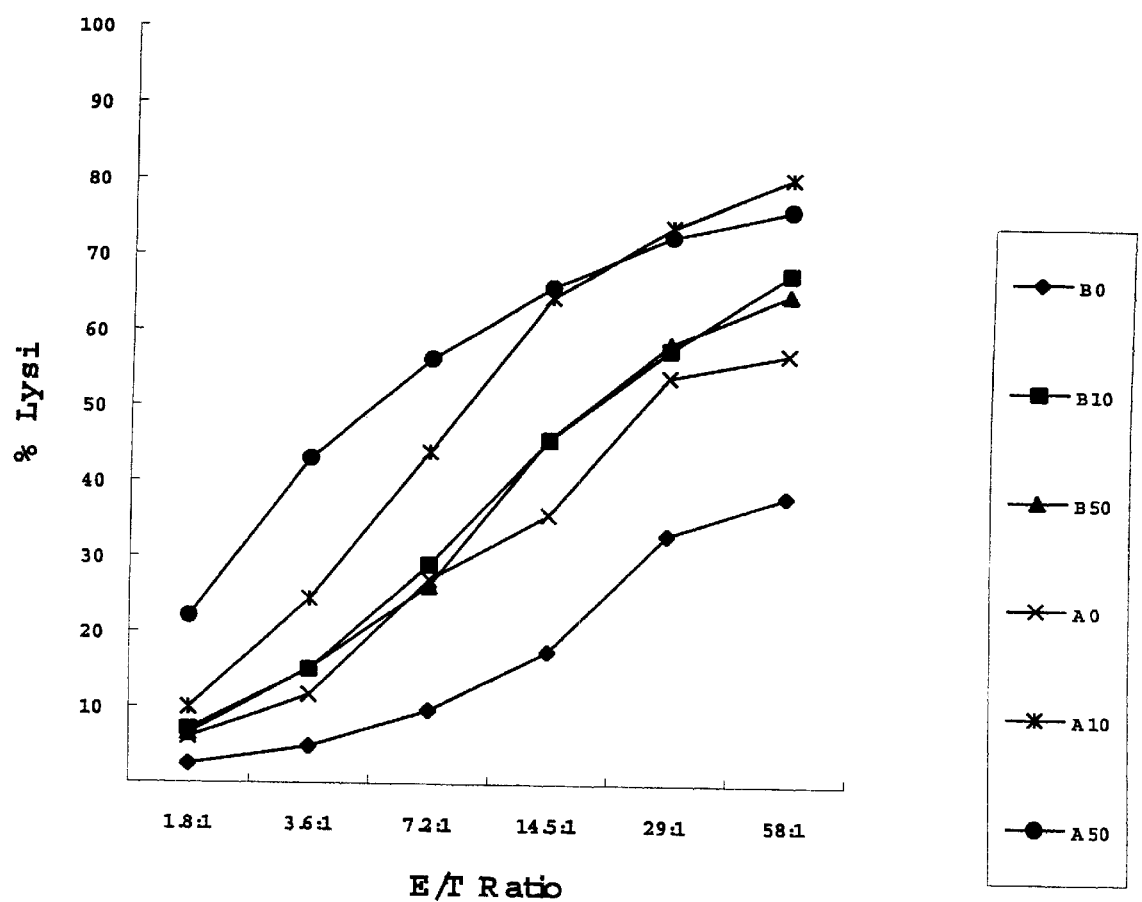
FIG. 8 shows the LAK activity of PBMC toward K562 cells. PBMC were isolated from volunteer before and after treatment with 1.5 g/Kg ST 188L orally for 7 days.

One healthy male volunteer's PBMC was collected, isolated and frozen at −70° C. on day 1. He started to intake ST 188L at the dosage of 1.5 g/Kg/day BID for 7 days. On day 8, his PBMC was collected and isolated. LAK activity was performed with Cr$^{51}$ release cytotoxicity assay by using Cr$^{51}$ labeled K562 cells as target. IL-2 at 10, 50 IU/ml was added in vitro for 3 days. The results were shown in FIG. 8 wherein the symbols indicate each of the following treatment groups: B0: PBMC isolated before in vivo treatment of 1.5 g/Kg ST 188L; B10: PBMC isolated before in vivo treatment of 1.5 g/Kg ST 188L+IL-2 (10 IU/ml) in vitro treatment for 3 days; B50: PBMC isolated before in vivo treatment of 1.5 g/Kg ST 188L+IL-2 (50 IU/mi) in vitro treatment for 3 days; A0: PBMC isolated after in vivo treatment of 1.5 g/Kg ST 188L for 7 days; A0: PBMC isolated after in vivo treatment of 1.5 g/Kg ST 188L for 7 days+IL-2 (10 IU/ml) in vitro treatment for 3 days; and A50: PBMC isolated after in vivo treatment of 1.5 g/Kg ST 188L for 7 days+IL-2 (50 IU/ml) in vitro treatment for 3 days. The lytic units were as follow in Table 16.

TABLE 16

Lytic units of PBMC treated with ST 188L in vivo on K562 cells

| Treatment | Lytic Unit | % of Control |
|---|---|---|
| Before ST 188L intake | | |
| Control | 87.0 | 100 |
| IL-2, 10 IU/ml | 421.2 | 484 |
| IL-2, 50 IU/ml | 390.5 | 449 |
| After ST 188L intake | | |
| Control | 281.4 | 323 |
| IL-2, 10 IU/ml | 507.9 | 584 |
| IL-2, 50 IU/ml | 1567.5 | 1802 |

As readily shown in Table 16, before intake of ST 188L, in vitro incubation of IL-2 at 10 or 50 IU/ml increased LAK activity to the same degree. After intake of ST 188L at 1.5 g/Kg/day, BID, the baseline activity increased 3.23 folds (from 87.0 to 281.4), and, in addition, IL-2 increased LAK activity in a dose responded manner.

(B. 4. 7) LAK Activity Against Human Hepatitis B Virus (HBV) Transfected Cells by Orally Administered ST 188L After In Vitro Incubation with IL-2.

Figure 9:
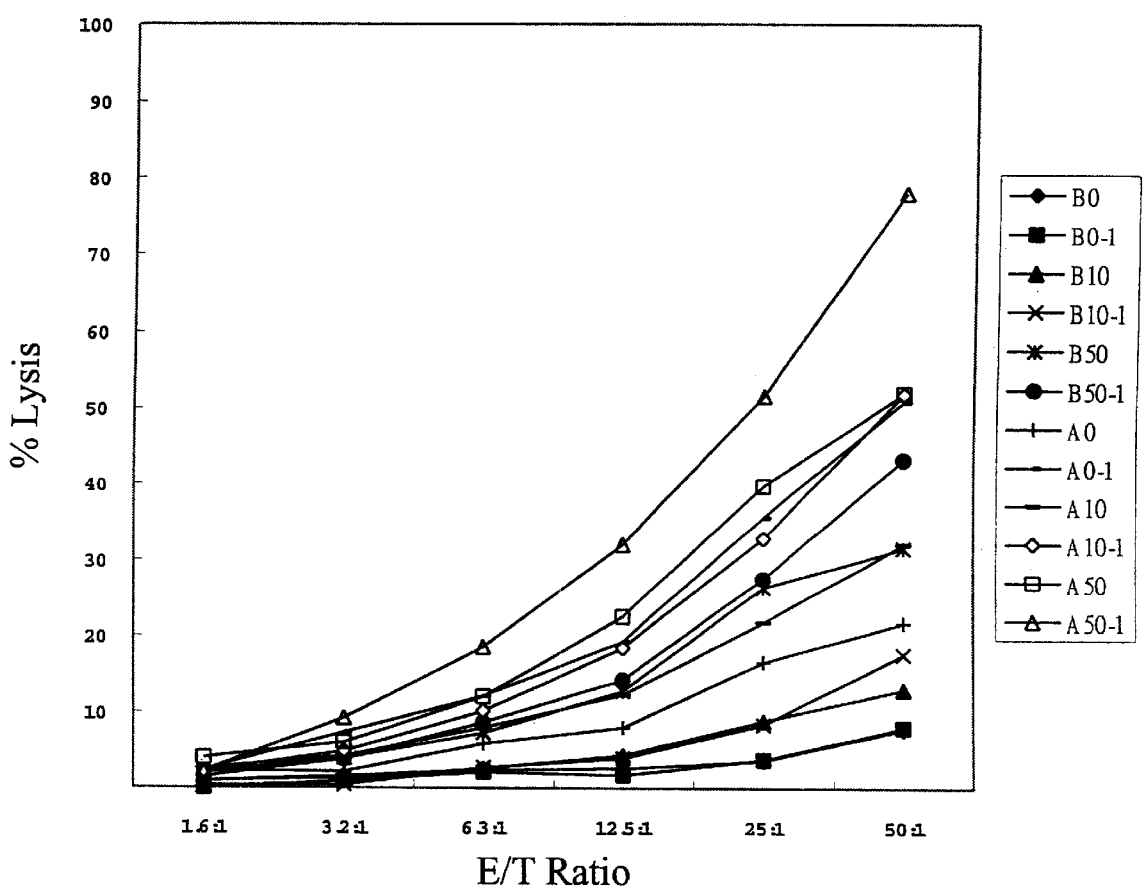
FIG. 9 shows the LAK activity of PBMC of volunteer before and after treatment of ST 188L orally toward parental and HBV transfected HepG2 cells.
Figure 10:
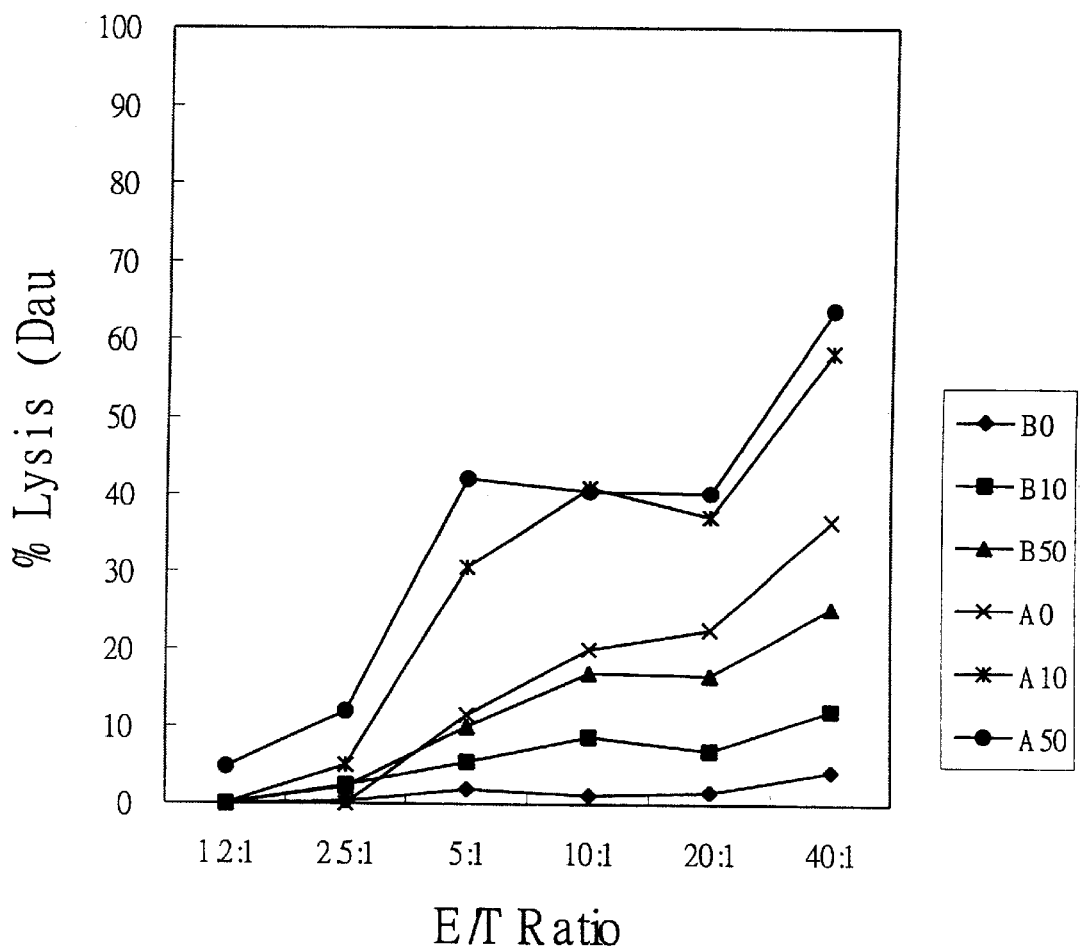
FIG. 10 shows the LAK activity of PBMC of volunteer before and after treatment of ST 188L orally toward Daudi cells.

One healthy male volunteer's PBMC was collected, isolated and frozen at −70° C. on day 1. He started to intake ST 188L at the dosage of 0.75 g/Kg/day, BID, for 7 days. On day 8, his PBMC was collected and isolated. LAK activity was performed with Cr$^{51}$ release cytotoxicity assay by using Cr$^{51}$ labeled parental HepG2, HBV transfected HepG2-2215, or Daudi cells as target. IL-2 at 10 or 50 IU/ml was incubated with PBMC in vitro for 7 days before assay. The results were shown in FIG. 9 (HepG2 and HepG2-2215 as targets) wherein the symbols indicate each of the following treatment groups: B0: HepG2 cells as target wherein Effector cells that were PBMC isolated before in vivo treatment of ST 188L at 0.75 g/Kg for 7 days were incubated without IL-2 in vitro for 7 days; B0-1: HepG2-2215 cells as target wherein Effector cells that were PBMC isolated before in vivo treatment of ST 188L at 0.75 g/Kg for 7 days were incubated without IL-2 in vitro for 7 days; B 10: HepG2 cells as target wherein Effector cells that were PBMC isolated before in vivo treatment of ST 188L at 0.75 g/Kg for 7 days were incubated with IL-2 at 10 IU/ml in vitro for 7 days; B0-1: HepG2-2215 cells as target wherein Effector cells that were PBMC isolated before in vivo treatment of ST 188L at 0.75 g/Kg for 7 days were incubated with IL-2 at 10 IU/ml in vitro for 7 days; B50: HepG2 cells as target wherein Effector cells that were PBMC isolated before in vivo treatment of ST 188L at 0.75 g/Kg for 7 days were incubated with IL-2 at 50 IU/ml in vitro for 7 days; B50-1: HepG2-2215 cells as target wherein Effector cells that were PBMC isolated before in vivo treatment of ST 188L at 0.75 g/Kg for 7 days were incubated with IL-2 at 50 IU/ml in vitro for 7 days; A0: HepG2 cells as target wherein Effector cells that were PBMC isolated after in vivo treatment of ST 188L at 0.75 g/Kg for 7 days were incubated without IL-2 in vitro for 7 days; A0-1: HepG2-2215 cells as target wherein Effector cells that were PBMC isolated after in vivo treatment of ST 188L at 0.75 g/Kg for 7 days were incubated without IL-2 in vitro for 7 days; A10: HepG2 cells as target wherein Effector cells that were PBMC isolated after in vivo treatment of ST 188L at 0.75 g/Kg for 7 days were incubated with IL-2 at 10 IU/ml in vitro for 7 days; A10-1: HepG2-2215 cells as target wherein Effector cells that were PBMC isolated after in vivo treatment of ST 188L at 0.75 g/Kg for 7 days were incubated with IL-2 at 10 IU/ml in vitro for 7 days; A50: HepG2 cells as target wherein Effector cells that were PBMC isolated after in vivo treatment of ST 188L at 0.75 g/Kg for 7 days were incubated with IL-2 at 50 IU/ml in vitro for 7 days; A50-1: HepG2-2215 cells as target wherein Effector cells that were PBMC isolated after in vivo treatment of ST 188L at 0.75 g/Kg for 7 days were incubated with IL-2 at 50 IU/ml in vitro for 7 days; HepG2: hepatocarcinoma cell line; and HepG2-2215: HepG2 cells transfected with human hepatitis B virus (HBV) and FIG. 10 (Daudi as target) wherein the symbols indicate each of the following treatment groups: B0: Daudi cells as target wherein Effector cells that were PBMC isolated before in vivo treatment of ST 188L at 0.75 g/Kg for 7 days were incubated without IL-2 in vitro for 7 days; B10: Daudi cells as target wherein Effector cells that were PBMC isolated before in vivo treatment of ST 188L at 0.75 g/Kg for 7 days were incubated with IL-2 at 10 IU/ml in vitro for 7 days; B50: Daudi cells as target wherein Effector cells that were PBMC isolated before in vivo treatment of ST 188L at 0.75 g/Kg for 7 days were incubated with IL-2 at 50 IU/ml in vitro for 7 days; A0: Daudi cells as target wherein Effector cells that were PBMC isolated after in vivo treatment of ST 188L at 0.75 g/Kg for 7 days were incubated without IL-2 in vitro for 7 days; A10: Daudi cells as target wherein Effector cells that were PBMC isolated after in vivo treatment of ST 188L at 0.75 g/Kg for 7 days were incubated with IL-2 at 10 IU/ml in vitro for 7 days; A50: Daudi cells as target wherein Effector cells that were PBMC isolated after in vivo treatment of ST 188L at 0.75 g/Kg for 7 days were incubated with IL-2 at 50.

The results demonstrated that volunteer's LAK cells in PBMC recognized HBV transfected HepG2-2215 preferentially when compared the cytolytic effects on parental and HBV transfected targets. After intake of ST 188L, the cytolytic effects of LAK cells in PBMC on HBV transfected targets further increased. The results in FIG. 10 demonstrated that the activity induced by ST 188L indeed was LAK activity by targeting at Daudi cells. It is concluded that ST 188L indeed increases the cytolytic effect of LAK cells toward HBV transfected HepG2-2215 cells. ST 188L clearly demonstrates anti-viral effect by enhancing LAK activity of the host.

(B. 4. 8)-NK Activity Against HBV Transfected Cells by Orally Administered ST 188L.

Figure 11:
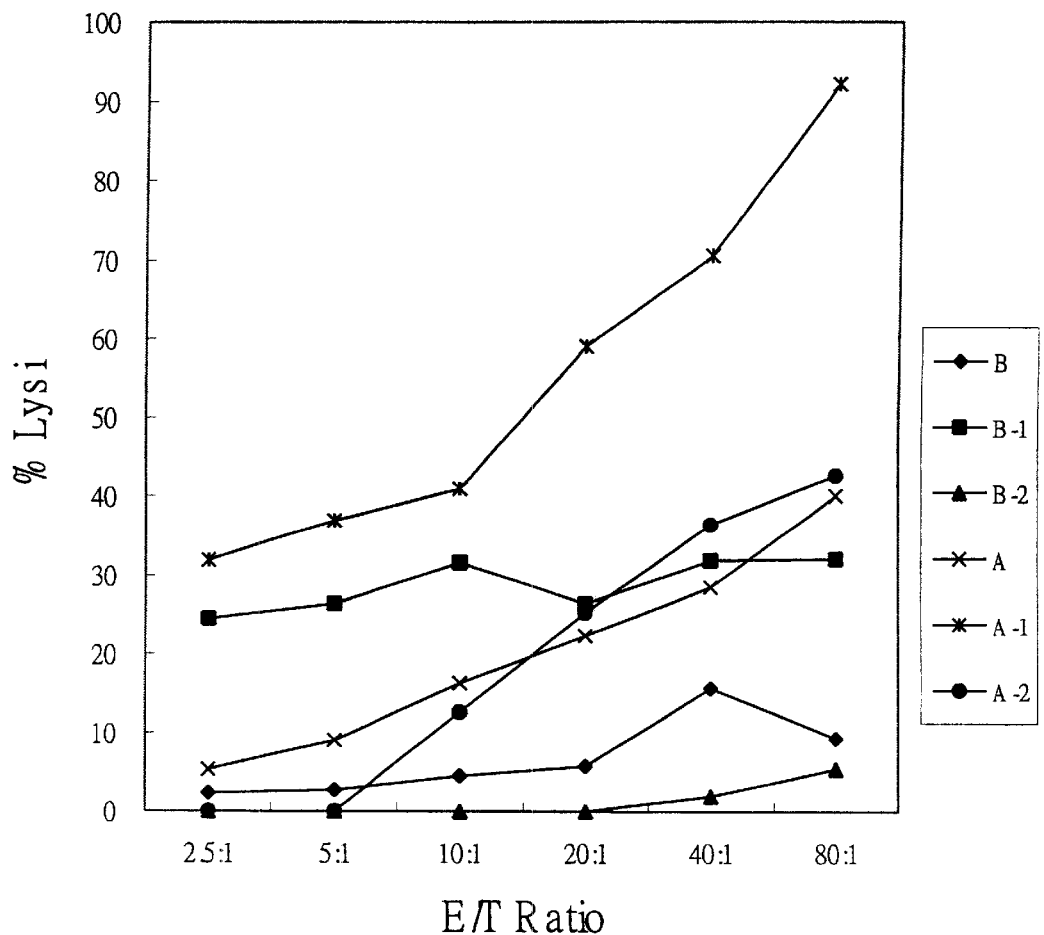
FIG. 11 shows the NK activity of PBMC of volunteer before and after treatment of ST 188L orally toward parental, HBV transfected HepG2 cells and K562 cells.

One healthy male volunteer's PBMC was collected, isolated and frozen at −70° C. on day 1. He started to intake ST 188L at the dosage of 0.75 g/Kg/day, BID, for 7 days. On day 8, his PBMC was collected and isolated. NK activity was performed with $Cr^{51}$ release cytotoxicity assay by using $Cr^{51}$ labeled HepG2, HBV transfected HepG2-2215, or K562 cells as target. The results were shown in FIG. 11 wherein the symbols indicate each of the following treatment groups: B: HepG2 cells as target wherein Effector cells were PBMC isolated before in vivo treatment of ST 188L at 0.75 g/Kg for 7 days; B-1: HepG2-2215 cells as target wherein Effector cells were PBMC isolated before in vivo treatment of ST 188L at 0.75 g/Kg for 7 days; B-2: K562 cells as target wherein Effector cells were PBMC isolated before in vivo treatment of ST 188L at 0.75 g/Kg for 7 days; A: HepG2 cells as target wherein Effector cells were PBMC isolated after in vivo treatment of ST 188L at 0.75 g/Kg for 7 days; A-1: HepG2-2215 cells as target wherein Effector cells were PBMC isolated after in vivo treatment of ST 188L at 0.75 g/Kg for 7 days; A 2: K562 cells as target wherein Effector cells were PBMC isolated after in vivo treatment of ST 188L at 0.75 g/Kg for 7 days; HepG2: Hepatocarcinoma cell line and HepG2-2215: HepG2 cells transfected with human hepatitis B virus (HBV).

The results demonstrated that volunteer's NK cells in PBMC recognized HBV transfected HepG2-2215 preferentially when compared the cytolytic effects on parental with HBV transfected targets. After intake of ST 188L, the cytolytic effects of NK cells in PBMC on HBV transfected targets further increased. The results demonstrated that the activity induced by ST 188L indeed was NK activity by targeting at K562 cells. In conclusion, ST 188L increases the cytolytic effect of NK cells toward HBV transfected HepG2-2215 cells. ST 188L clearly demonstrates anti-viral effect by enhancing NK activity of the host.

(B. 5)-In Vivo, ST 188L Treatment on Cancer Patient.

Patient T (female, age 41) was diagnosed with nasopharyngeal squamous cell carcinoma in 1989. Patient T was surgically excised the left nasal tumor and left medial maxillectomy via midfacial degloving. Radiotherapy was given at 7650 rads in three months after surgery. Four months later, tumor was found recurrent locally. Bilateral partial maxillectomy was performed. Two months later, another tumor extirpation was performed to remove tumor at posterior wall of left maxillary antrum, anterior to tubal cushion of left Eustachian tube, orifice and soft palate. The pathohistology of excised tissue specimen were studied. Microscopically, nests of non-keratinized squamous cell carcinoma were observed over the fibromuscular tissue. This was diagnosed as recurrent invasive squamous cell carcinoma. The patient started to take ST 188L orally at the dose of 1.5 g/Kg/day after having exhausted all the western medical treatment options. Two months later, the patient was followed up in the hospital by biopsy. Microscopically, it showed granulation tissue composed mainly of acute inflammation, proliferative capillaries and edematous stroma. No evidence of recurrent malignancy was found. Eight months later, the patient was followed up in the hospital by head CT scan. It showed increased density at left ethmoid, sphenoid and maxillary sinuses, and intact orbital cavity. One month later, the patient was followed up in the hospital by biopsy. Microscopically, it showed granulation tissue. No malignancy was found. Two months later, the patient was followed up in the hospital by biopsy. Microscopically, it showed granulation tissue with capillary proliferation within the edematous stroma. Plasma cell and lymphocyte infiltration within the stroma, and ulceration on the surface were found. No malignancy was found. Plasma cell and lymphocyte infiltration indicated that the immune system of the patient was activated. The patient is currently living healthily and working since she was diagnosed with NPC more than 10 years ago.

In summary, ST 188L has been proven clinically to be effective on eradicating malignancy in cancer patients by enhancing patients' endogenous immune system to keep patients cancer free for more than ten years. The underlying mechanisms of ST 188L's effects are revealed in this invention.

ST 188L was not toxic in vitro and was not toxic in vivo up to 19.8 g/Kg in rats. Their anti-cancer activity mechanisms observed clinically was due to its immune modulation activity after metabolic activation in vivo.

ST 188L incubated with K562 cells in vitro did not significantly modify K562 cells to become more susceptible to NK cells. In vitro treatment of PBMC with ST 188L somehow decreased its LAK activity. Thus, ST 188L appeared to be activated in vivo to stimulate the activity of NK cells and LAK cells as shown by the increases in cytolytic activity of PBMC isolated from volunteers after intake of ST 188L toward K562 and Daudi target cells in a dose dependent manner. Intake of ST 188L also potentiated IL-2's activity dose dependently.

The activation of NK and LAK activities by in vivo ST 188L administration can treat and prevent the occurrence, recurrence and metastasis of cancers, since NK and LAK cells are the first line of immune surveillance in vivo against cancers.

As evident by many researches that NK cells are involved in anti-infectious agent defenses, this invention showed that orally administered ST 188L increased the cytolytic effects of LAK and NK cells in PBMC preferentially toward HBV transfected HepG2-2215 cells compared to the parental HepG2 cells. ST 188L very likely would have anti-viral effect in vivo by enhancing LAK and NK activity of the host. The activation of NK and LAK activities by ST 188L in vivo may have activity in prevention and treatment of infectious agent, such as virus, bacteria, protozoa, and parasite infections.

What is claimed is:

1. A pharmaceutical composition for treating nasopharyngeal carcinomas comprising effective amounts of *Echlinops grijissii, Cirsium segetum* Bge, *Solanum indicum* Linn, *Lonicerae flos*, and *Zizyphi fructus* in a pharmaceutically acceptable carrier or diluent.

2. The pharmaceutical composition of claim 1 wherein said *Echinops grijissii, Cirsium segetum* Bge, *Solanum indicum* Linn, *Lonicerae flos*, and *Zizyphi fructus* are present respectively in a dried, weight-to-weight range of about 5–15:2–6:2–6:1–10:1–5.

3. The pharmaceutical composition of claim 2 wherein said weight-to-weight range is 5:2:2:1:1.

4. The pharmaceutical composition of claim 1 wherein the composition is prepared in a form of a tablet, soft gel, granule, powder, liquid, capsule or honey ball.

5. The pharmaceutical composition of claim 4 wherein the powder form is further formulated with an additive selected from the group consisting of lactose, starch, acicel, priomojel, prejel, sodium cross carmellose, hydroxymethylcellulose, hydroxypropylcellulose, PVP and magnesium stereate to form a medicine dosage form.

6. A pharmaceutical composition for enhancing endogenous immune system of a recipient by activation of said recipient's natural killer cells and lymphokine activated killer cells comprising effective amounts of *Echinops grijissii, Cirsium segetum* Bge, *Solanum indicum* Linn, *Lonicerae flos*, and *Zizyphi fructus* in a pharmaceutically acceptable carrier or diluent.

7. The pharmaceutical composition of claim 6 wherein said *Echinops grijissii, Cirsium segetum* Bge, *Solanum indicum* Linn, *Lonicerae flos*, and *Zizyphi fructus* are present respectively in a dried, weight-to-weight range of about 5–15:2–6:2–6:1–10:1–5.

8. The pharmaceutical composition of claim 7 wherein said weight-to-weight range is 5:2:2:1:1.

9. The pharmaceutical composition of claim 6 wherein the formulation is prepared in a form of a tablet, soft gel, granule, powder, liquid, capsule or honey ball.

10. The pharmaceutical composition of claim 9 wherein the powder form is further formulated with an additive selected from the group consisting of lactose, starch, acicel, priomojel, prejel, sodium cross carmellose, hydroxymethylcellulose, hydroxypropylcellulose, PVP and magnesium stereate to form a medicine dosage form.

11. A pharmaceutical composition exhibiting anti-viral activity for treating human hepatitis B virus comprising effective amounts of *Echinops grijissii, Cirsium segetum* Bge, *Solanum indicum* Linn, *Lonicerae flos*, and *Zizyphi fructus* in a pharmaceutically acceptable carrier or diluent.

12. The pharmaceutical composition for treating human hepatitis B of claim 11 wherein said *Echinops grijissii, Cirsium segetum* Bge, *Solanum indicum* Linn, *Lonicerae flos*, and *Zizyphi fructus* are present respectively in a dried, weight-to-weight range of about 5–15:2–6:2–6:1–10:1–5.

13. The pharmaceutical composition for treating human hepatitis B of claim 12 wherein said weight-to-weight range is 5:2:2:1:1.

14. The pharmaceutical composition for treating human hepatitis B of claim 11 wherein the formulation is prepared in a form of a tablet, soft gel, granule, powder, liquid, capsule or honey ball.

15. The pharmaceutical composition for treating human hepatitis B of claim 14 wherein the powder form is further formulated with an additive selected from the group consisting of lactose, starch, acicel, priomojel, prejel, sodium cross carmellose, hydroxymethylcellulose, hydroxypropylcellulose, PVP and magnesium stereate to form a medicine dosage form.

* * * * *